United States Patent
Shin et al.

(10) Patent No.: US 6,630,593 B1
(45) Date of Patent: Oct. 7, 2003

(54) PROCESS FOR PREPARING A 1-SUBSTITUTED 5-HYDROXYMETHYL IMIDAZOLE

(75) Inventors: Hyun-Ik Shin, Daejeon (KR); Jay-Hyok Chang, Daejeon (KR); Kyoo-Woong Lee, Daejeon (KR); Hyun-Il Lee, Daejeon (KR); Sung-Kee Kim, Daejeon (KR); Do-Hyun Nam, Daejeon (KR)

(73) Assignee: LG Chem Investment Ltd., Seoul (KR)

( * ) Notice: Subject to any disclaimer, the term of this patent is extended or adjusted under 35 U.S.C. 154(b) by 0 days.

(21) Appl. No.: 10/070,511

(22) PCT Filed: Sep. 6, 2000

(86) PCT No.: PCT/KR00/01016
§ 371 (c)(1),
(2), (4) Date: Mar. 5, 2002

(87) PCT Pub. No.: WO01/17974
PCT Pub. Date: Mar. 15, 2001

(30) Foreign Application Priority Data

Sep. 6, 1999 (KR) ........................................ 1999/37652
Jan. 28, 2000 (KR) ........................................ 2000/4278

(51) Int. Cl.⁷ ...................... C07D 233/64; C07D 233/84
(52) U.S. Cl. .................................. 548/311.7; 548/341.1
(58) Field of Search ............................ 548/311.7, 341.1

(56) References Cited

U.S. PATENT DOCUMENTS 4,111,948 A   9/1978   Kao et al.

FOREIGN PATENT DOCUMENTS

| DE | 33 40 932 | 5/1985 |
|----|-----------|--------|
| EP | 0 146 228 | 10/1984 |
| WO | WO 99/05117 | 2/1999 |
| WO | WO99/05117 A1 * | 2/1999 |
| WO | WO 00/01674 | 1/2000 |
| WO | WO-00/01674 A1 * | 1/2000 |

OTHER PUBLICATIONS

Aulaskari, P. et al., "Preparation and Structure Determination of 1-Benzyl-, 1-Methyl-and 1H-50 [(2-Nitro-2-phnyl) ethenyl] imidazoles," J. Heterocyclic Chem., vol.33, 1996, pp. 1345–1354.

Dener, J.M., et al., "An Effective Chirospecific Synthesis of (+) Pilocarpine from L-Aspartic Acid," J. Org. Chem., vol. 58, 1993, pp. 1159–1166.

Meanwall, N.A., et al., "Nonprostanoid Prostacyclin Mimetics. 3. Structural Variations of the Diphenyl Heterocycle Moiety," J. Ned. Chem., vol. 35, 1992, pp. 3498–3512.

Duncia, J.V., et al., "The Discovery of Potent Nonpeptide Angiotensin II Receptor Antagonists: A New Class of Potent Antihypertensives," J. Med. Chem., 1990, pp. 1312–1329.

* cited by examiner

*Primary Examiner*—Laura L. Stockton
(74) *Attorney, Agent, or Firm*—Peter F. Corless; John B. Alexander; Edwards & Angell, LLP

(57) ABSTRACT

A process for preparing a 1-substituted 5-hydroxymethylimidazole of the formula:

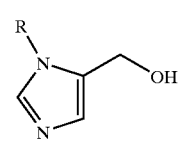

(1)

, wherein R represents alkyl, hydroxyalkyl, allyl, or substituted or unsubstituted arylmethyl or diarylmethyl, comprising the step of reacting a 1-substituted 2-mercapto-5-hydroxymethylimidazole of the formula:

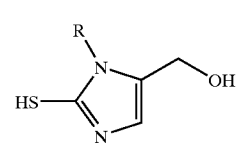

(2)

, wherein R is as defined above, in the presence of a transition metal catalyst and an oxidizing agent in a solvent.

14 Claims, No Drawings

PROCESS FOR PREPARING A 1-SUBSTITUTED 5-HYDROXYMETHYL IMIDAZOLE

TECHNICAL FIELD

The present invention relates to a process for preparing a 1-substituted 5-hydroxymethylimidazole of the formula:

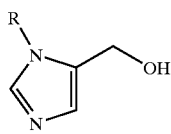
(1)

, wherein
R represents alkyl, hydroxyalkyl, allyl, or substituted or unsubstituted arylmethyl or diarylmethyl, and preferably, $C_{1-4}$alkyl, hydroxy$C_{1-4}$alkyl, allyl, benzyl, substituted benzyl such as halogen-substituted benzyl or 3,4-dioxymethylenebenzyl, or 2-arylmethyl.

More specifically, the present invention relates to a process for preparing compound of the above formula (1) from a 1-substituted 2-mercapto-5-hydroxymethylimidazole of the formula:

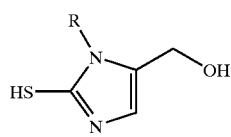
(2)

, wherein R is as defined above, which is prepared by reacting 1,3-dihydroxyacetone dimer of the formula:

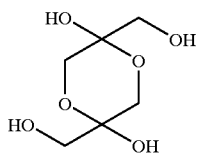
(3)

, with an acid addition salt of amine of the formula:

RNH$_2$ (4)

, wherein R is as defined above, and thiocyanate of the formula:

M—SCN (5)

, wherein M represents alkali metal, in the presence of a transition metal catalyst such as tungstic acid, etc. and an oxidizing agent.

BACKGROUND ART

The 1-substituted 5-hydroxymethylimidazole of the formula (1) and its intermediate, i.e. 1-substituted 2-mercapto-5-hydroxymethylimidazole of the formula (2) are key intermediates known to be useful for preparing various anticancer agents under development, especially, farnesyl transferase inhibitors[J. S. Ko, et al., PCT WO99/05 1 17 A1 19990204, p129].

Various processes for the preparation of the compound of the formula (2) have already been known in the literature. For example, according to the process disclosed in E-P 146228B1, 1985, the 1-substituted 2-mercapto-5-hydroxymethylimidazole is obtained in the yield of 68.2% as a pale brown powder by reacting 1,3-dihydroxyacetone dimer of the formula:

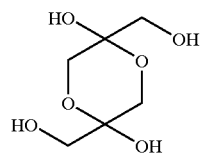
(3)

, as the starting material, with amine of the formula:

RNH$_2$ (4)

, wherein R represents alkyl, allyl, arylmethyl or diarylmethyl, and thiocyanate of the formula:

M—SCN (5)

, wherein M represents potassium,
in the mixture of an organic acid and a lower alcohol solvent.

However, under the above reaction conditions, there are some problems associated with the isolation of the product in good purity since an unidentified black tar is formed as a by-product and turned out to be difficult to purify.

For preparing compound of the formula (1) from compound of the formula (2), the known process, an oxidative desulfurization is conventionally performed by warming compound of the formula (2) in the presence of concentrated nitric acid, with or without the catalytic amount of nitrite[R. G. Jones, J. Amer. Chem. Soc., 1949, 71, 383]. This method is useful in the laboratory scale preparation. However, this process has some problems associated with safety in the industrial scale. These are evolution of environmentally toxic nitrogen oxide gas and difficult control of the reaction. In addition, if the compound of the formula (2) has an aromatic functionality, electrophilic aromatic nitration reaction on the aromatic ring is accompanied as a side reaction.

DISCLOSURE OF THE INVENTION

The present inventors performed extensive studies to develop a novel process for the preparation of a 1-substituted 5-hydroxymethylimidazole and its intermediate, a 1-substituted 2-mercapto-5-hydroxymethylimidazole. As a result, they have identified that the problems of the previous process for preparing compound of the formula (2) could be removed by replacing amine by its acid addition salt. That is, if the acid addition salt of amine such as ammonium chloride is used, the formation of the colored by-products are eradicated completely. Therefore, the desired compound, compound of the formula (2) can be obtained in high purity and yield.

In addition, since there are few practical examples of oxidative cleavage of thiol group, which allows to prepare compound of the formula (1) from compound of the formula (2), the present inventors made a research to develop a new process which could be viable in the industrial scale. Finally, they have identified that the desired imidazole derivative can be obtained in high purity under safe and environmentally benign reaction conditions by employing a transition metal catalyst and an oxidizing agent such as hydrogen peroxide and thus, completed the present invention.

DETAILED DESCRIPTION OF THE INVENTION

Therefore, an object of the present invention is to provide a new process for the preparation of a 1-substituted 5-hydroxymethylimidazole of the formula (1) from 1-substituted 2-mercapto-5-hydroxymethyl imidazole of the formula (2).

The present invention relates to a process for preparing 1-substituted 5-hydroxymethylimidazole of the formula:

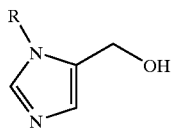
(1)

, wherein R represents alkyl, hydroxyalkyl, allyl, or substituted or unsubstituted arylmethyl or diarylmethyl, and preferably, $C_{1-4}$alkyl, hydroxy$C_{1-4}$alkyl, allyl, benzyl, substituted benzyl such as halogen-substituted benzyl or 3,4-dioxymethylenebenzyl, or 2-arylmethyl, comprising the steps of reacting 1,3-dihydroxyacetone dimer of the formula:

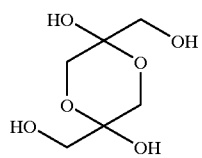
(3)

, with an acid addition salt of amine of the formula:

RNH$_2$  (4)

, wherein R is as defined above, and thiocyanate of the formula:

M—SCN  (5)

, wherein M represents alkali metal, in the presence of an acid catalyst in a lower alcohol solvent to prepare a 1-substituted 2-mercapto-5-hydroxymethylimidazole of the formula:

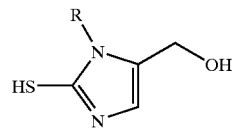
(2)

, wherein R is as defined above; and,
reacting the compound of the formula (2) in the presence of a transition metal catalyst and an oxidizing agent in a solvent.

As for the substituent "R", however, any conventional substituents other than those as mentioned above may be applied without any explicit indication.

The term "alkyl" as used herein includes straight or branched chain alkyl.

The preparation process according to the present invention comprises 2 steps. The first step is that a 1-substituted 2-mercapto-5-hydroxymethylimidazole of the formula (2) is prepared by reacting 1,3-dihydroxyacetone dimer of the formula (3) with an acid addition salt of amine of the formula (4) and thiocyanate of the formula (5). The second step is that a 1-substituted 5-hydroxymethylimidazole of the formula (1) is prepared from the above compound of the formula (2) via oxidative desulfurization.

Therefore, the present invention relates to a process for preparing a 1-substituted 5-hydroxymethylimidazole of the formula:

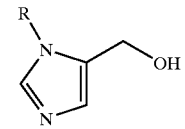
(1)

, wherein R is as defined above,
by the reaction of compound of the formula:

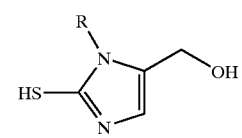
(2)

, wherein R is as defined above,
in the presence of a transition metal catalyst and an oxidizing agent in a solvent.

Hereinafter, each step of the present process will be explained in detail.

In Step 1, a 1-substituted 2-mercapto-5-hydroxymethylimidazole of the formula

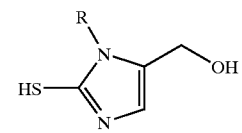
(2)

, wherein R is as defined above,
is prepared by reacting 1,3-dihydroxyacetone dimer of the formula:

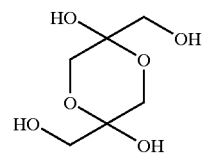
(3)

, with an acid addition salt of amine of the formula:

RNH$_2$  (4)

, wherein R is as defined above, and thiocyanate of the formula:

M—SCN  (5)

, wherein M is as defined above,
in the presence of an acid catalyst in a lower alcohol solvent.

The above reaction is depicted in the following Reaction Scheme (1):

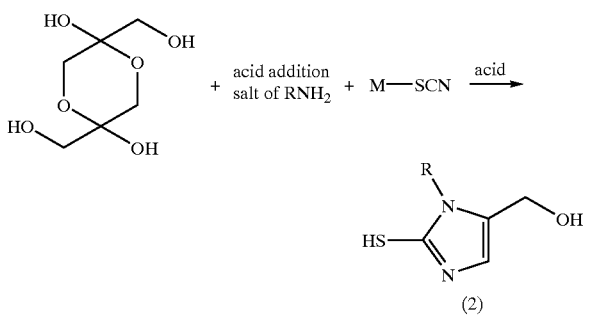

, wherein M and R are each as defined above.

The formation mechanism of imidazole compound of the formula (2) is depicted below(vide infra). Iminium intermediate is formed from dihydroxyacetone and amine, and tautomerized to α-aminoaldehyde intermediate, which reacts with thiocyanate to give urea intermediate. Intramolecular cyclization and dehydration should afford compound of the formula (2).

Reaction Scheme (2)

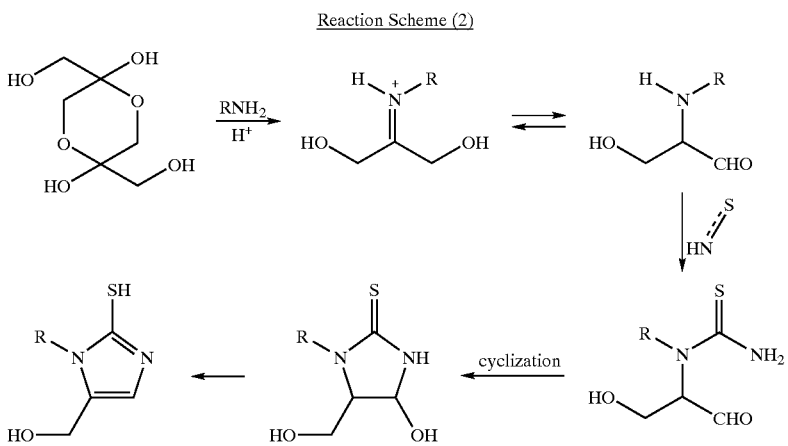

In the above reaction scheme, R is as defined above.

Since it is assumed that impurity material should be formed by the reaction of reactive α-aminoaldehyde intermediate and excessive amine, control of the concentration of free amine in a suitable level is thought to be the key factor for clean reaction. Therefore, in the present invention, the problems of the previous method are removed by lowering the concentration of free amine by the employment of an acid addition salt of amine.

More specifically, to prepare a 1-substituted 2-mercapto-5-hydroxymethylimidazole of the formula (2), 1,3-dihydroxyacetone dimer of the formula (3), an acid addition salt of amine of the formula (4) and thiocyanate of the formula (5) are mixed in a mixture of lower alcohol and organic acid.

In the above reaction, the molar ratio of the 1,3-dihydroxyacetone dimer of the formula (3) to the acid addition salt of amine of the formula (4) is 0.5~2:1, preferably, 1~1.5:1. The molar ratio of the thiocyanate of the formula (5) to the acid addition salt of amine of the formula (4) is 1~3:1, preferably, 1~2:1.

As the acid addition salt of amine of the formula (4) in the above reaction, on ammonium halide is preferable and ammonium chloride is most preferable. In addition., as thiocyanate of the formula (5), potassium thiocyanate is preferable.

The acid addition salt of amine of the formula (4) in the above reaction may be commercially available or prepared with ease according to the known procedure. In some cases, it can be prepared by introducing hydrohalogen gas into amine in an equimolar amount.

As the reaction solvent, straight or branched chain lower alcohol having from 1 to 4 carbon atom(s), or a mixture thereof is preferable. More preferably, iso-propanol or n-butanol may be used.

As the reaction catalyst, acetic acid, propionic acid or any other conventional organic acids may be used preferably.

The reaction temperature may be 10 to 100° C., preferably 20 to 80° C.

In Step 2, a 1-substituted 5-hydroxymethylimidazole of the formula:

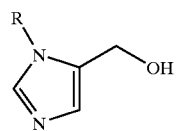

, wherein R is as defined above,
is prepared by reacting a 1-substituted 2-mercapto-5-hydroxymethylimidazole of the formula:

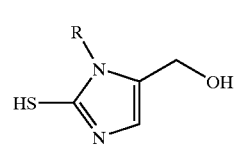

, wherein R is as defined above,
in the presence of a transition metal catalyst and an oxidizing agent such as hydrogen peroxide, etc. in a solvent.

The above reaction step is explained more specifically as follows.

A 1-substituted 2-mercapto-5-hydroxymethylimidazole of the formula (2) is reacted in the presence of oxidizing agent and the catalytic amount of transition metal in water, any other aqueous solvent or a mixture thereof at room temperature or the elevated temperature. In accordance with the above process, the 1-substituted 2-mercapto-5-hydroxymethylimidazole can be converted into a 1-substituted 5-hydroxymethyl imidazole of the formula (1) with ease.

As the catalyst to be used in the above step, several transition metals with oxidizing ability such as vanadium, chromium, molybdenum, manganese, tungsten, rhenium, ruthenium, osmium, etc. may be used. Among them, rhenium, ruthenium, osmium, etc. have a drawback due to their high cost, and vanadium, chromium, manganese, tungsten, etc. are preferable because of their relatively low cost. More preferable is tungstic acid ($H_2WO_4$), vanadium pentoxide ($V_2O_5$) or vanadyl sulfate ($VOSO_4$) The molar ratio of the transition metal catalyst such as tungstic acid ($H_2WO_4$), vanadium pentoxide ($V_2O_5$) or vanadyl sulfate ($VOSO_4$) to the compound of the formula (2) is generally 0.001~0.2:1, preferably 0.001~0.02:1.

As the useful oxidizing agent in the present invention, hydrogen peroxide, alkyl hydrogen peroxide(such as t-butyl hydrogen peroxide etc.) or alkaline hypochlorite (sodium or calcium salt) is preferable. More preferable is 10~30% hydrogen peroxide They are used in an amount of 3 to 10 molar equivalents with respect to compound of the formula (1).

As the reaction solvent, water or any other aqueous solvent, preferably, lower alcohol or a mixture thereof may be used. The most preferable is water, methanol, ethanol or a mixture thereof.

The reaction temperature may be 20 to 100° C., preferably 40 to 70° C., more preferably 50 to 70° C. Generally, the reaction is performed until a 1-substituted 2-mercapto-5-hydroxymethylimidazole of the formula (2) is completely converted into a 1-substituted 5-hydroxymethylimidazole of the formula (1), preferably, for 2 to 6 hours.

Upon the completion of the reaction, the reaction mixture may be simply neutralized and then, the resulting solid may be filtered. Alternatively, the reaction mixture may be extracted with a suitable solvent such as dichloromethane or chloroform and if necessary, further purified by treatment with a suitable solvent such as n-hexane or isopropyl ether Accordingly, the desired compound, i.e., 1-substituted 5-hydroxymethylimidazole of the formula (1) may be easily recovered from the reaction mixture in high purity.

This invention will be better understood from the following examples. However, one skilled in the art will readily appreciate the specific materials and results described are merely illustrative of, and are not intended to, nor should be intended to, limit the invention as described more fully in the claims which follow thereafter.

<Step 1: Synthesis of a 1-Substituted 2-mercapto-5-hydroxymethyl-imidazole>

EXAMPLE 1

Synthesis of 1-Benzyl-2-mercapto-5-hydroxymethylimidazole

Benzylammonium chloride(14.36 g, 0.1 mol) and 1,3-dihydroxyacetone dimer(18 g, 0.1 mol) were suspended in 100 ml of isopropanol and then, potassium thiocyanate(14.6 g, 0.15 mol) was added thereto. To the above suspension was added dropwise acetic acid(19.22 g, 0.32 mol) and the mixture was stirred at room temperature for 24 hours. To the above mixture was added 50 ml of distilled water. The whole mixture was further stirred for 30 minutes, filtered and washed twice with 50 ml of distilled water and 50 ml of isopropyl ether, respectively, to obtain a white solid powder. The obtained powder was dried for 3 hours to give 20.4 g(Yield 92.6%) of 1-benzyl-2-mercapto-5-hydroxymethylimidazole.

$^1$H NMR (500 MHz, DMSO-$d_6$) δ 12.15 (1H, s), 7.32 (2H, t, J=7.3 Hz), 7.26 (1H, d, J=7.3 Hz), 7.24 (2H, t, J=7.3 Hz), 6.85 (1H, s), 5.32 (2H, s), 5.25 (1H, s), 4.14 (2H, d, J=5 Hz); HPLC: 99.6%

EXAMPLE 2

Synthesis of 1-Ethyl-2-mercapto-5-hydroxymethylimidazole

Ethylammonium chloride(8.16 g, 0.1 mol) and 1,3-dihydroxyacetone dimer(18 g, 0.1 mol) were suspended in 70 ml of isopropanol and then, potassium thiocyanate(14.6 g, 0.15 mol) was added thereto. To the above suspension was added dropwise acetic acid(19.22 g, 0.32 mol) and the mixture was stirred at room temperature for 24 hours To the above reaction solution was added 50 ml of distilled water. The whole mixture was further stirred for 30 minutes, filtered and washed twice with 50 ml of distilled water and 50 ml of isopropyl ether, respectively, to obtain a white solid powder. The obtained powder was dried for 3 hours to give 12.8 g(Yield 81.0%) of 1-ethyl-2-mercapto-5-hydroxymethylimidazole.

$^1$H NMR (500 MHz, DMSO-$d_6$) δ 11.94 (1H, s) 6.78 (1H, s) 5.20 (1H, s, —OH) 4.33 (2H, s) 4.00 (2H, q, J=7.2 Hz) 1.21 (3H, t, J=7.2 Hz);

HPLC: 99.1%

EXAMPLES 3~5

Synthesis of 2-Mercaptoimidazole Derivatives

Several 2-mercaptoimidazole derivatives were synthesized according to the substantially same procedure as Example 1. The results were shown in the following Table 1.

TABLE 1

2-mercaptoimidazole derivatives

| Ex. No. | R | Reaction Time | Yield | ¹H NMR |
|---|---|---|---|---|
| 3 | 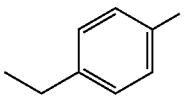 | 15 | 91% | 12.18(1H, s) 7.51(2H, d, J=8.7Hz) 7.20(2H, d, J=8.7Hz) 6.86(1H, s) 5.28(2H, s and 1H; —OH) 5.16(2H, d, J=3.7Hz) |
| 4 | 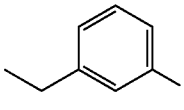 | 15 | 88% | 12.20(1H, s) 7.45(1H, d, J=7.8Hz) 7.44(1H, s) 7.29(1H, t, J=7.8Hz) 7.22(1H, d, J=7.8Hz) 6.88(1H, s) 5.81(2H, s and 1H, s, —OH) 4.17(2H, s) |
| 5 | 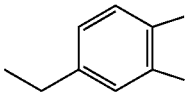 | 22 | 96% | 12.16(1H, s) 6.89(1H, d, J=1.8Hz) 6.85(1H, d, J=7.8Hz) 6.83(1H, s) 6.75(1H, dd, J1=7.8Hz, J2=1.8Hz) 5.98(2H, s) 5.31(1H, s, —OH) 5.21(2H, s) 4.17(2H, s) |

EXAMPLE 6

Synthesis of 1-Allyl-2-mercapto-5-hydroxymethylimidazole

Allylammonium chloride(0.1 mol) was reacted for 23 hours according to the substantially same procedure as Example 1. Then, 40 ml of distilled water was added thereto and the reaction mixture was distilled under reduced pressure to ⅓ volume. The precipitate was filtered, washed twice with 30 ml of distilled water and 30 ml of isopropyl ether, respectively, and dried to give 12.5 g(Yield 72.6%) of the title compound as a white powder.

$^1$H NMR (500 MHz, DMSO-$d_6$) δ 12.03 (1H, s), 6.81 (1H, s), 5.89 (1H, m), 5.21 (1H, —OH), 5.12 (1H, dd, $J_1$=10.5 Hz, $J_2$=1.4 Hz), 4.97 (1H, dd, $J_1$=14.4 Hz, $J_2$=1.4 Hz), 4.67 (2H, s), 4.28 (2H, s)

EXAMPLE 7

Synthesis of 1-(3-Hydroxypropyl)-2-mercapto-5-hydroxymethylimidazole

The title compound was obtained in the yield of 69% according to the substantially same procedure as Example 1. The $^1$H NMR data are as shown below.

$^1$H NMR (500 MHz, DMSO-$d_6$) δ 11.96 (1H, s), 6.80 (1H, s), 5.19 (1H, —OH), 4.56 (1H, —OH), 4.35 (2H, s), 4.02 (2H, t, 7.3 Hz), 3.40 (2H, m), 1.85 (2H, t, J=7.3 Hz)

<Step 2: Synthesis of a 1-Substituted 5hydroxymethylimidazole>

EXAMPLE 8

Synthesis of 1-Benzyl-5-hydroxymethylimidazole

1-Benzyl-2-mercapto-5-hydroxymethylimidazole(2.2 g, 9.99 mmol) and tungstic acid($H_2WO_4$, 25 mg, 1 mol %) were mixed in 11 ml of methanol. The mixture was warmed to 40° C. in a water bath and 30% hydrogen peroxide(3.75 g, 3.2 molar eq.) was added dropwise thereto for 5 minutes while stirring. The reaction mixture was warmed to 65° C. and refluxed, and stirred at the same temperature for 2.5 hours. Upon exhaustion of the starting material, the mixture was cooled in an ice bath and thereto was added 1 N sodium hydroxide solution(18 ml) to adjust pH of the mixture to 10. The resulting solid was further stirred for 15 minutes, filtered, washed twice with 15 ml of distilled water and 15 ml of isopropyl ether, respectively, and dried to give 1.3 g(Yield 69%, HPLC purity 96.7%) of the title compound as a white powder.

$^1$H NMR (500 MHz, DMSO-$d_6$) δ 7.67 (1H, s), 7.35 (2H, t, J=7.3 Hz), 728 (1H, t. J=7.3 Hz), 7.17 (2H, d, J=7.3 Hz), 6.82 (1H, s), 5.23 (2H, s), 5.11 (1H, t, —OH), 4.32 (2H, d, J=5.5 Hz); $^{13}$C NMR (125 MHz, DMSO-$d_6$) δ 163.15, 137.68, 130.91, 128.97, 127.78, 127.40, 113.39, 53.88, 46.97.

EXAMPLE 9

Synthesis of 1-(4-Bromobenzyl)-5-hydroxymethylimidazole 1-(4-Bromobenzyl)-2-mercapto-5-hydroxymethylimidazole(1.5 g, 5 mmol) and tungstic acid (12.5 mg, 1 mol %) were suspended in 7 ml of methanol. The suspension was warmed to 40° C. and then, 30% hydrogen peroxide was slowly added dropwise. After about 2 hours, the mixture was cooled and neutralized with 1 N sodium hydroxide solution, and the precipitate was filtered. The obtained solid was washed twice with 5 ml of distilled water and 5 ml of isopropyl ether, respectively, to give 1.1 g(Yield 82%) of the title compound as a white powder.

$^1$H NMR (500 MHz, DMSO-$d_6$) δ 7.68 (1H, s), 7.54 (2H, dd, $J_1$=6.4 Hz, $J_2$=1.8 Hz), 7.12 (2H, dd, $J_1$=6.4 Hz, $J_2$=1.8 Hz), 6.83 (1H, s), 5.21 (2H, s), 5.12 (1H, s, —OH), 4.32 (2H, d, $J_{gem}$=3.25 Hz) $^{13}$C NMR (125 MHz, DMSO-$d_6$) δ 139.04, 137.66, 132.07, 129.83, 128.08, 121.22, 113.75, 53.33, 47.45.

EXAMPLE 10

Synthesis of 1-(3-Bromobenzyl)-5-hydroxymethylimidazole

The title compound was obtained in the yield of 75% by employing 1-(3-bromobenzyl)-2-mercapto-5-hydroxymethylimidazole according to the substantially same procedure as Example 9.

$^1$H NMR (500 MHz, DMSO-$d_6$) δ 7.71 (1H, s), 7.49 (1H, d, J=7.8 Hz), 7.37 (1H, s), 7.31 (1H, t, J=7.8 Hz), 7.16 (1H, d, J=7.8 Hz), 6.84 (1H, s), 5.24 (sH, s), 5.13 (1H, s, —OH), 4.32 (2H, d, J$_{gem}$=4.6 Hz); $^{13}$C NMR (125 MHz, DMSO-d$_6$) δ 141.02, 139.11, 132.14, 131.34, 130.96, 130.31 128.08, 126.67, 124.42, 53.28,47.35

EXAMPLE 11

Synthesis of 1-(3,4-Dioxymethylenebenzyl)-5-hydroxymethylimidazole 1-(3,4-Dioxymethylenebenzyl)-2-mercapto-5-hydroxymethylimidazole (2.64 g, 10 mmol) and vanadium pentoxide(V$_2$O$_5$, 18 mg, 1 mol %) were suspended in 10 ml of ethanol and 10 ml of distilled water. The suspension was warmed to about 50° C. and 30% hydrogen peroxide was slowly added dropwise thereto. After about 1 hour, the mixture was cooled and thereto was added 1 N sodium hydroxide solution to adjust the pH of the mixture to 10. The resulting mixture was filtered, washed twice with 15 ml of distilled water and 15 ml of isopropyl ether, respectively, and dried to give 2.05 g(Yield 88%) of the title compound as a white powder.

$^1$H NMR (500 MHz, DMSO-d$_6$) δ 7.64 (1H, s), 6.87 (1H, d, J=7.5 Hz), 6.79 (2×1H, s), 6.70 (1H, d, J=7.5 Hz), 5.99 (2H, s), 5.10 (2H, s and 1H, s, —OH), 4.34 (2H, s); $^{13}$C NMR (125 MHz, DMSO-d$_6$) δ 148.06, 147.23, 138.82, 132.09, 131.84, 127.93, 121.28, 108.80, 108.40, 101.62, 53.34, 47.87.

EXAMPLE 12

Synthesis of 1-Ethyl-5-hydroxymethylimidazole

The title compound was obtained in the yield of 68% by employing 1-ethyl-2-mercapto-5-hydroxymethylimidazole according to the substantially same procedure as Example 8 except that the residue was extracted with chloroform instead of being filtered.

$^1$H NMR (500 MHz, DMSO-d$_6$) δ 7.59 (1H, s), 6.76 (1H, s), 4.43 (2H, 2), 3.99 (2H, q, J=7.3 Hz), 1.33 (3H, t, J=7.3 Hz); $^{13}$C NMR (125 MHz, DMSO-$_6$) δ 137.83, 131.85, 127.69, 60.92, 53.15, 16.93.

EXAMPLE 13

Synthesis of 1-Allyl-5-hydroxymethylimidazole

The title compound was obtained in the yield of 76% by employing 1-allyl-2-mercapto-5-hydroxymethylimidazole according to the substantially same procedure as Example 8 except that the residue was extracted with n-butanol instead of being filtered.

$^1$H NMR (500 MHz, DMSO-d$_6$) δ 7.54 (1H, s), 6.79 (1H, s), 6.00 (1H, ddd, J$_1$=20 Hz, J$_2$=10 Hz, J$_3$=5.5 Hz), 6.15 (1H, dd, J$_1$=10 Hz, J$_2$=1.35 Hz), 4.98 (1H, dd, J$_1$=16.95 Hz, J$_2$=1.35 Hz), 4.64 (2H, dd, J$_1$=5.5 Hz, J$_2$=1.35 Hz), 4.39 (2H, s); $^{13}$C NMR (125 MHz, DMSO-d$_6$) δ 138.47, 135.15, 132.19, 127.72, 117.37, 60.91, 47.07.

EXAMPLE 14

Synthesis of 1-(3-Hydroxypropyl)-5-hydroxymethylimidazole 1-(3-Hydroxypropyl)-2-mercapto-5-hydroxymethylimidazole(5.0 g, 23.1 mmol) and tungstic acid(H$_2$WO$_4$, 58 mg, 1 mol %) were mixed in 25 ml of methanol and 25 ml of distilled water. The mixture was warmed to 40° C. and 3.6 g of 30% hydrogen peroxide was added dropwise thereto. The whole mixture was stirred for 15 minutes and cooled and then, neutralized with 1 N sodium hydroxide solution. The resulting mixture was extracted twice with 25 ml of n-butanol and the solvent was distilled under reduced pressure to give 3.45 g(Yield 80.7%) of the title compound. $^1$H NMR (500 MHz, CDCl$_3$) δ 7.46 (1H, s), 6.91 (1H, s), 4.61 (2H, s), 4.15 (2H, t, J=7 Hz), 3.52 (2H, t, J=7 Hz), 2.01 (2H, m).

EXAMPLE 15

Synthesis of 1-(4-bromobenzyl)-5-hydroxymethylimidazole 1-(4-Bromobenzyl)-2-mercapto-5-hydroxymethylimidazole(40 g, 0.134 mol) and vanadyl sulfate hydrate(21.9 mg, 0.1 mol %) were introduced into a mixed solution of 240 ml of ethanol and 240 ml of water. The mixture was warmed to 45° C. and stirred. After a short time, 30% hydrogen peroxide(51.6 g, 3.4 molar eq.) was slowly added dropwise thereto and the internal temperature was kept at about 50° C. When the initial white suspension turned to a pale yellow solution, the solution was further stirred for about 30 minutes to which was added 6 N sodium hydroxide solution to adjust pH of the solution to about 10. Then, ethanol was distilled under reduced pressure The precipitated crystal was filtered, washed with distilled water and dried to the constant weight to give 28.7 g(Yield 80.4%, HPLC=97%) of the title compound as a white powder.

$^1$H NMR (δ, ppm, DMSO-d$_6$) 7.68 (1H, s), 7.54 (2H, d, J=8.3 Hz), 7.12 (2H, d, J=8.3 Hz), 6.82 (1H, s), 5.21 (2H, s), 5.09 (1H, t, J=5.5 Hz), 4.31 (2H, s).

EXAMPLE 16

Synthesis of 1-(3,4-Dioxymethylenebenzyl)-5-hydroxymethylimidazole 1-(3,4Dioxymethylenebenzyl)-2-mercapto-5-hydroxymethylimidazole(22.15 kg 83.8 mol) and vanadyl sulfate hydrate(11 g, 0.1 mol %) were introduced into the reactor 47.1 kg of Ethanol and 55 kg of purified water were added thereto and the temperature of the reaction solution was adjusted to 44° C. while stirring. To the above suspension was slowly added 32.2 kg of 30% hydrogen peroxide at the temperature ranging from 40 to 60° C. The whole mixture was stirred at 46° C. and 6 N sodium hydroxide solution was added thereto to adjust pH of the mixture to 10. Then, ethanol was distilled under reduced pressure. Upon completion of the distillation, the residue was cooled to room temperature, filtered, washed with purified water, and dried to give 11.5 kg(Yield 59. 9%, HPLC=96.6%) of the title compound as a pale yellow powder.

$^1$H NMR (δ, ppm, DMSO-d$_6$) 7.64 (1H, s), 6.87 (1H, d, J=7.8 Hz), 6.79 (2H, s), 6.69 (1H, d, J=7.8 Hz), 5.99 (2H, s), 5.10 (2H, s), 4.34 (2H, s).

INDUSTRIAL APPLICABILITY

As described above, the 1-substituted 5-hydroxymethylimidazole of the formula (1) and the 1-substituted 2-mercapto-5-hydroxymethyl-imidazole of the formula (2) prepared according to the present process are known to be useful intermediates for preparing anticancer agents, farnesyl transferase inhibitors[J. S. Ko, et al., PCT WO99/05117 A1 19990204, p129].

According to the present process, the 1-substituted 2-mercapto-5-hydroxymethylimidazole of the formula (2) can be more safely and rapidly prepared in higher purity and yield, as compared with the conventional preparation process. In addition, the 1-substituted 5-hydroxymethylimidazole of the formula (1) can be prepared in high yield and purity under safe reaction condition via oxidative elimination of the thiol group. Accordingly, the present process is applicable in the industrial scale preparation, since it can be safely performed without use of concentrated nitric acid.

What is claimed is:

1. A process for preparing a 1-substituted 5-hydroxymethylimidazole of the formula:

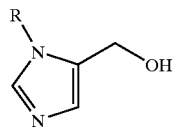 (1)

wherein R represents alkyl, hydroxyalkyl, allyl, or substituted or unsubstituted arylmethyl or diarylmethyl, comprising the step of reacting a 1-substituted 2-mercapto-5-hydroxymethylimidazole of the formula:

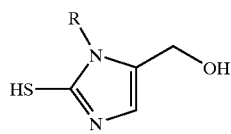 (2)

wherein R is as defined above,
in the presence of a transition metal catalyst and an oxidizing agent in a solvent.

2. The process of claim 1, wherein the oxidizing agent is selected from the group consisting of hydrogen peroxide, alkyl hydrogen peroxide and alkaline hypochlorite.

3. The process of claim 2, wherein the oxidizing agent is 10~30% hydrogen peroxide.

4. The process of claim 1, wherein the transition metal catalyst is selected from the group consisting of tungstic acid($H_2WO_4$), vanadium pentoxide($V_2O_5$) and vanadyl sulfate($VOSO_4$).

5. The process of claim 1, wherein the molar ratio of the transition metal catalyst to the compound of the formula (2) is 0.001~0.2:1.

6. The process of claim 1, wherein the solvent is selected from the group consisting of water, lower alcohol and a mixture thereof.

7. The process of claim 1, wherein the 1-substituted 2-mercapto-5-hydroxymethylimidazole of the formula (2) is prepared by reacting 1,3-dihydroxyacetone dimer of the formula:

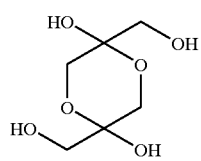 (3)

, with an acid addition salt of amine of the formula:

 (4)

, wherein R is as defined in claim 1, and
thiocyanate of the formula:

 (5)

, wherein M represents alkali metal,
in the presence of an acid catalyst in a lower alcohol solvent.

8. The process of claim 7, wherein M represents potassium.

9. The process of claim 7, wherein the acid addition salt of amine is ammonium halide.

10. The process of claim 9, wherein the ammonium halide is ammonium chloride.

11. The process of claim 7, wherein the molar ratio of the 1,3-dihydroxyacetone dimer of the formula (3) to the acid addition salt of amine of the formula (4) is 0.5~2:1.

12. The process of claim 7, wherein the molar ratio of the thiocyanate of the formula (5) to the acid addition salt of amine of the formula (4) is 1~3:1.

13. The process of claim 7, wherein the lower alcohol is isopropanol or n-butanol.

14. The process of claim 1 or 7, wherein R represents $C_{1-4}$alkyl, hydroxy$C_{1-4}$alkyl, allyl, benzyl, halogen-substituted benzyl or 3,4-dioxymethylenebenzyl.

* * * * *